(12) United States Patent
Lazarus et al.

(10) Patent No.: US 8,410,562 B2
(45) Date of Patent: Apr. 2, 2013

(54) METHODS, APPARATUSES, AND SYSTEMS FOR MICROMECHANICAL GAS CHEMICAL SENSING CAPACITOR

(75) Inventors: Nathan Lazarus, Pittsburgh, PA (US); Gary Fedder, Turtle Creek, PA (US); Sarah Bedair, Bethesda, MD (US); Chiung Lo, Campbell, CA (US)

(73) Assignee: Carnegie Mellon University, Pittsburgh, PA (US)

(*) Notice: Subject to any disclaimer, the term of this patent is extended or adjusted under 35 U.S.C. 154(b) by 134 days.

(21) Appl. No.: 13/010,954

(22) Filed: Jan. 21, 2011

(65) Prior Publication Data
US 2011/0180884 A1    Jul. 28, 2011

Related U.S. Application Data

(60) Provisional application No. 61/336,532, filed on Jan. 22, 2010.

(51) Int. Cl.
*H01L 27/14* (2006.01)

(52) U.S. Cl. . 257/414; 257/532; 257/535; 257/E29.324; 257/E21.613; 438/49; 438/50; 438/52; 438/53

(58) Field of Classification Search ............ 257/414, 257/532, 535, E29.324, E21.613; 438/49, 438/50, 52, 53
See application file for complete search history.

(56) References Cited

U.S. PATENT DOCUMENTS

| | | | |
|---|---|---|---|
| 5,349,493 A | 9/1994 | Winsor, IV | |
| 5,970,315 A | 10/1999 | Carley et al. | |
| 5,972,722 A | 10/1999 | Visokay et al. | |
| 6,087,701 A * | 7/2000 | Bergstrom et al. | 257/414 |
| 6,171,865 B1 | 1/2001 | Weigl et al. | |
| 6,628,501 B2 | 9/2003 | Toyoda | |
| 6,850,859 B1 | 2/2005 | Schuh | |
| 7,061,061 B2 | 6/2006 | Goodman et al. | |
| 7,147,764 B2 | 12/2006 | Vann et al. | |
| 7,151,659 B2 | 12/2006 | Kao et al. | |
| 7,273,779 B2 | 9/2007 | Fishburn et al. | |
| 7,338,802 B2 | 3/2008 | Frischauf et al. | |
| 7,378,313 B2 | 5/2008 | Zheng | |
| 2002/0158293 A1* | 10/2002 | Lee et al. | 257/414 |
| 2003/0002238 A1 | 1/2003 | Toyoda | |
| 2006/0237310 A1 | 10/2006 | Patel et al. | |
| 2011/0045601 A1* | 2/2011 | Gryska et al. | 436/149 |

FOREIGN PATENT DOCUMENTS

EP    1607739 A1    12/2005

OTHER PUBLICATIONS

Alfeeli et al., Multi-inlet/outlet Preconcentrator with a 3-D µ-Structures Coated by Inkjet Printing of Tenax TA, Solid-State Sensors, Actuators, and Microsystems Workshop, Jun. 1-5, 2008, 118-121.

(Continued)

*Primary Examiner* — Kimberly Rizkallah
*Assistant Examiner* — Maria Ligai
(74) *Attorney, Agent, or Firm* — The Web Law Firm

(57) ABSTRACT

A capacitive chemical sensor, along with methods of making and using the sensor are provided. The sensors described herein eliminate undesirable capacitance by etching away the substrate underneath the capacitive chemical sensor, eliminating most of the substrate capacitance and making changes in the chemical-sensitive layer capacitance easier to detect.

20 Claims, 15 Drawing Sheets

OTHER PUBLICATIONS

Bedair et al., Polymer Wicking to Mass Load Cantilevers for Chemical Gravimetric Sensors, Transducers, 2005, 2035-2039.

Chang et al., Charge-Based Capacitance Measurement for Bias-Dependent Capacitance, IEEE Electron Device Letters, May 2006, 390-392, vol. 27, No. 5.

Fedder, MEMS Fabrication, Proceedings of the ITC International Test Conference, 2003, 691-698, paper 27.3.

Fedder et al., Laminated high-aspect-ratio microstructures in a conventional CMOS process, Sensors and Actuators A, 1996, 103-110, vol. 57.

Fedder et al., Laminated High-Aspect-Ratio Microstructures in a Conventional CMOS Process, IEEE, 1996, 13-18.

Hierlemann, CMOS-based Chemical Sensors in Advanced Micro and Nanosystems, col. 2 CMOS-MEMS, Eds. Baltes et al., 2005, Wiley-VCH, Weinheim, Germany.

Patel et al., Chemicapacitive microsensors for volatile organic compound detection, Sensors and Actuators B, 2003, 541-553, vol. 96.

Wang et al., Humidity sensors based on silica nanoparticle aerogel thin films, Sensors and Actuators B, 2005, 402-410, vol. 107.

Weiss et al., Inkjet Deposition System with Computer Vision-Based Calibration for Targeting Accuracy, Technical Report CMU-RI-TR-06-15, Mar. 2006, 1-12.

Yao et al., A capacitive humidity sensor based on gold-PVA core-shell nanocomposites, Sensors and Actuators B, 2010, 327-333, vol. 145.

* cited by examiner

METHODS, APPARATUSES, AND SYSTEMS FOR MICROMECHANICAL GAS CHEMICAL SENSING CAPACITOR

CROSS-REFERENCE TO RELATED APPLICATIONS

This application claims the benefit of U.S. Provisional Application No. 61/336,532, filed Jan. 22, 2010, which is incorporated herein by reference in its entirety.

STATEMENT REGARDING FEDERALLY-SPONSORED RESEARCH AND DEVELOPMENT

This invention was made with partial government support under NIOSH/CDC 200-2002-00528 and AFOSR FA9550-07-1-0245. The government has certain rights in this invention.

This invention relates generally to the field of chemical sensing. In particular, it relates to methods for improving the sensitivity of capacitive chemical sensors integrated with testing electronics.

Capacitive chemical sensors have traditionally been made by creating a bottom electrode, depositing a sensitive material, and then patterning a set of top electrodes (also referred to herein as conductors. A diagram of this structure 10 is shown in FIG. 1, showing silicon 12 and silicon dioxide 14 substrate layers, electrodes 16 and 17 and chemical-sensitive polymer layer 18. In reference to the Figures, electrodes that are numbered differently refer to opposite conductors (+versus −, as the case may be) in the capacitor structure. The silicon dioxide layer serves as a dielectric, electrically insulating, layer that is not sensitive to exposure to chemicals. Many other insulating materials can serve this purpose. The silicon layer serves as a mechanical substrate. Many other materials can also serve this purpose. This structure has high sensitivity, since all the electric field lines must pass through the sensitive material. Using polyimide polymer, sensitivities reported when this method is applied to humidity sensing are approximately 0.2% change in capacitance for every 1% change in relative humidity. However, this structure is difficult to integrate with testing electronics; placing a sensitive layer between two metal layers requires significant processing beyond conventional CMOS, and has not been successfully demonstrated.

As a result, other capacitive sensors have used an alternative approach, coating interdigitated metal electrodes with a sensitive film. This sensor 20 is shown in FIG. 2, which depicts silicon 22 and silicon dioxide 24 substrate layers, electrodes 26 and 27 and chemical-sensitive polymer 28. This simplifies processing, by eliminating the necessity of having metal above and below the sensitive layer, but at a cost of creating a large, parallel capacitance through the substrate under the electrodes. A technique developed by Seacoast (United States Patent Publication No. 2006/0237310) raises the electrodes on a short vertical post, but vertical posts are also difficult to integrate with CMOS processing.

A variant of this approach, developed by ETH Zurich (European Patent Publication EP 1 607 739 A1), leaves the oxide in CMOS in place, coating the top surface of a foundry CMOS chip; this simplifies fabrication, but further reduces the sensitivity since the most direct electric field lines pass through the oxide. A simplified diagram of this approach is shown in FIG. 3, depicting a sensor 30, and showing silicon 32 and silicon dioxide 34 substrate layers, along with electrodes 36 and 37 and chemical-sensitive polymer 38. The sensing capacitance of the ETH Zurich device with polyurethane as the sensitive polymer is 1.4 pF in parallel with a substrate capacitance of 6.4 pF. Since 18% of the total capacitance is affected by the analyte, the sensitivity is at most 18% of that of a parallel plate sensor (such as in FIG. 1), or about 0.04% change in capacitance per percent relative humidity.

Another technique that has been used is to remove the underlying substrate, leaving the electrodes on a thin dielectric membrane (United States Patent Publication No. 2003/0002238 A1); a diagram is shown in FIG. 4. In FIG. 4, sensor 40 is shown, along with silicon 42, silicon dioxide 44, electrode 46 and 47 and chemical-sensitive polymer 48 structures. This has the effect of removing the parasitic capacitance between the electrodes and the substrate, but there will still be a parallel capacitance through the non-sensitive dielectric 44 that will degrade the sensitivity.

Accordingly, there is a need for improved methods, apparatuses, and systems for capacitance-based gas chemical sensing which reduce parasitic capacitance and are manufacturable through low cost methods.

SUMMARY

This present invention describes methods, apparatuses, and systems for improving the sensitivity of integrated capacitive chemical sensors by removing the underlying substrate. The sensor is integrated with CMOS testing electronics using mask-less post-processing followed by inkjet deposition of polymers that are sensitive to the analyte of interest. This approach provides improved sensing capabilities in a system that is easily manufactured.

A capacitive sensor is therefore provided. The sensor comprises a semiconductor substrate having a well; and one or more conductor pairs attached to the substrate at an attachment point and extending over the well, defining an air gap between the conductor pair and the substrate, each conductor pair comprising a first and second conductor spaced-apart to define a capillary gap. As used herein, a capillary gap is a gap having a width such that a solution comprising a chemical-sensitive dielectric material can be drawn between the conductors into the capillary gap by capillary action. The width of the capillary gap may vary depending on the overall structure or the conductors and the physical properties of the chemical-sensitive dielectric material. For example and without limitation, the capillary gap may be at least 1 µm wide, for instance, 2 µm wide. Unless specifically indicated, the term "pairs" does not imply that there are strictly an even number of conductors, only that there are one, two or more groupings of conductors that can form capacitors when a suitable chemical-sensitive dielectric material is deposited between the conductors. For example three conductors can produce two electrode pairs in a "+ − +" or "− + −" configuration. For example a "+ − +" configuration comprises a "+ −" and a "− +" electrode pair, with the "−" conductor being shared in both electrode pairs. As illustrated below, each conductor may comprise two or more metal layers separated by an insulator, such as the dielectrics silicon oxide, silicon dioxide, silicon nitride, silicon oxynitride and doped versions thereof, and two or more metal layers in each conductor of the conductor pair are electrically connected to each-other at one or more points.

The sensor comprises a chemical-sensitive dielectric material in the capillary gap. A chemical-sensitive dielectric material is a material (e.g., an absorbent dielectric material) that changes its dielectric properties in response to the absorption of a compound. One example of a chemical-sensitive dielectric material is a polyimide. Other examples include polymethyl methacrylate (PMMA), poly(ethylene teraphthalate) (PET), polysulfone (PSF), cellulose acetate butyrate (CAB), polyethynyl fluorenol (PEFI), poly(dimethyl siloxane (PDMS), poly(etherurethane) (PEUT) and a nanocomposite, such as a nanocluster or other nanoparticle-containing material, as well as a large variety of other materials, for example as indicated below.

According to one embodiment, each conductor of the one or more conductor pairs has an inward-facing side that faces the substrate and an outward-facing side opposite the inward-facing side, and the chemical-sensitive dielectric material covers the outward-facing side of the conductors. Alternately, or in combination with the above, the well may be partly or wholly filled with the chemical-sensitive dielectric material, such that the conductor pairs are embedded within the chemical-sensitive dielectric material or at least the inward-facing side of the conductor pairs is coated.

Although the geometry of the conductors and conductor pairs may vary greatly and is typically a matter of design choice, in one embodiment, as shown in the examples below, the conductors are linear beams suspended over the well, with "suspended" including cantilevered or otherwise supported in one or more places. The conductors may be any useful length, for example and without limitation at least 100 µm long, for example 150 µm or 350 µm in length. The sensor may comprise a plurality of conductor pairs (at least two, but including any useful number of pairs. Structures including long conductors and conductor pairs may require multiple support sites that can be built into the sensor structure. In one example, the sensor comprises a plurality of conductor pairs, wherein the plurality of conductor pairs that are supported by one or more trusses extending between the conductors and the conductor pairs.

The capillary gap may be filled by wicking from the end or by wicking from above or below the gap. In one embodiment, the capillary gap is filled from an end of the conductor pairs. In that embodiment, the substrate further comprises an inkjet well and the capillary gaps of the one or more conductor pairs opens into the inkjet well such that a solution comprising a chemical-sensitive dielectric material deposited into the inkjet well is drawn into the capillary gap.

A sensing apparatus comprising the sensor described above also is provided. In one embodiment the apparatus is contained in a gas mask (e.g., a respirator or other breathing mask) which is useful in indicating, for example, end of useful life of a filtration cartridge. The apparatus may comprise a sensor computing device including data amplification, retrieval and/or communication functions device connected electrically to the sensor for obtaining, storing and transferring data obtained from the sensor.

A method of making a capacitive sensor also is provided. The method comprising, wicking a chemical-sensitive dielectric material by capillary action into a capillary gap between conductors of one or more conductor pairs in a semiconductor sensor to produce a capacitive sensor, the sensor comprising a semiconductor substrate having a well, and the one or more conductor pairs attached to the substrate at an attachment point and extending over the well and defining an air gap between the conductor pairs and the substrate. Capillary action occurs where liquid flows into a narrow space such as a thin tube or gap, and in the context of the present disclosure, between two narrowly-spaced conductors. Capillary action draws a liquid into a narrow gap or tube due to inter-molecular attractive forces between a liquid and solid surrounding surfaces. As used herein the action of drawing a liquid into a sufficiently small gap by capillary action is referred to as "wicking." As above, the chemical-sensitive dielectric material may be any material useful for such purposes, but may be selected from the group consisting of polyimide, polymethyl methacrylate (PMMA), poly(ethylene teraphthalate) (PET), polysulfone (PSF), cellulose acetate butyrate (CAB), polyethynyl fluorenol (PEFI), poly(dimethyl siloxane (PDMS), poly(etherurethane) (PEUT) and a nanocomposite, such as a nanocluster or other nanoparticle-containing material. In one embodiment, each conductor of the one or more conductor pairs has an inward-facing side that faces the substrate and an outward-facing side opposite the inward-facing side, and the chemical-sensitive dielectric material is deposited by inkjet deposition on the outward-facing side of the conductors. In another embodiment, each conductor of the one or more conductor pairs has an inward-facing side that faces the substrate and an outward-facing side opposite the inward-facing side, the method further comprising depositing the chemical-sensitive dielectric material on the inward-facing side of the conductor pairs, for example by filling the well with the chemical-sensitive dielectric material to cover the conductor pairs with the chemical-sensitive dielectric material.

As illustrated below, each conductor may comprise two or more metal layers separated by an insulator, such as the dielectrics silicon oxide, silicon dioxide, silicon nitride, silicon oxynitride and doped versions thereof, and two or more metal layers in each conductor of the conductor pair are electrically connected to each-other at one or more points.

As above, the conductors may be beams suspended over the well that are, for example at least 100 µm long, for example and without limitation, 150 or 350 µm long. In one embodiment, the sensor comprises a plurality of conductor pairs, wherein the plurality of conductor pairs are supported by one or more trusses extending between the conductors and the conductor pairs.

As indicated above, the capillary gap may be filled with the chemical-sensitive dielectric material by wicking from the end of the conductors or from the inward- or outward-facing surfaces of the conductors. In one non-limiting embodiment, the substrate further comprises an inkjet well, the capillary gaps of the one or more conductor pairs opens into the inkjet well and the chemical-sensitive dielectric material is deposited into the inkjet well and is drawn into the capillary gap.

BRIEF DESCRIPTION OF THE DRAWINGS

FIG. 5 is a cross section diagram of an embodiment of the sensor described herein showing effects of removing the substrate beneath a chemical sensitive capacitor.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

Figure 5A:
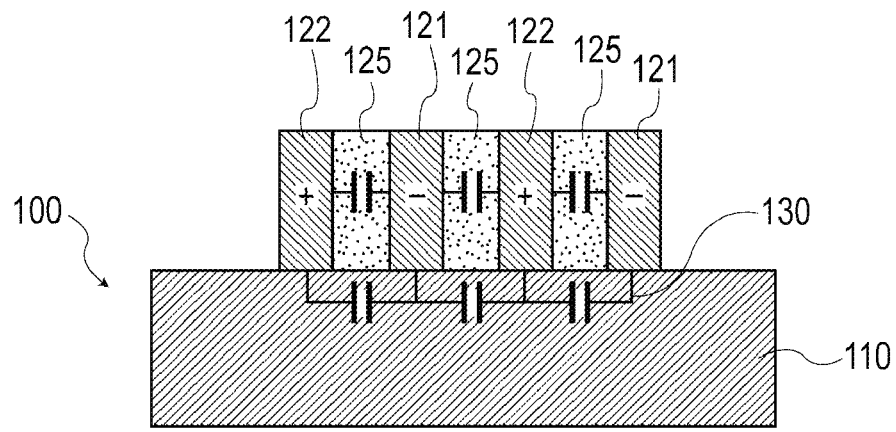
FIG. 5A shows an interdigitated structure, with large capacitances through the substrate.
Figure 5B:
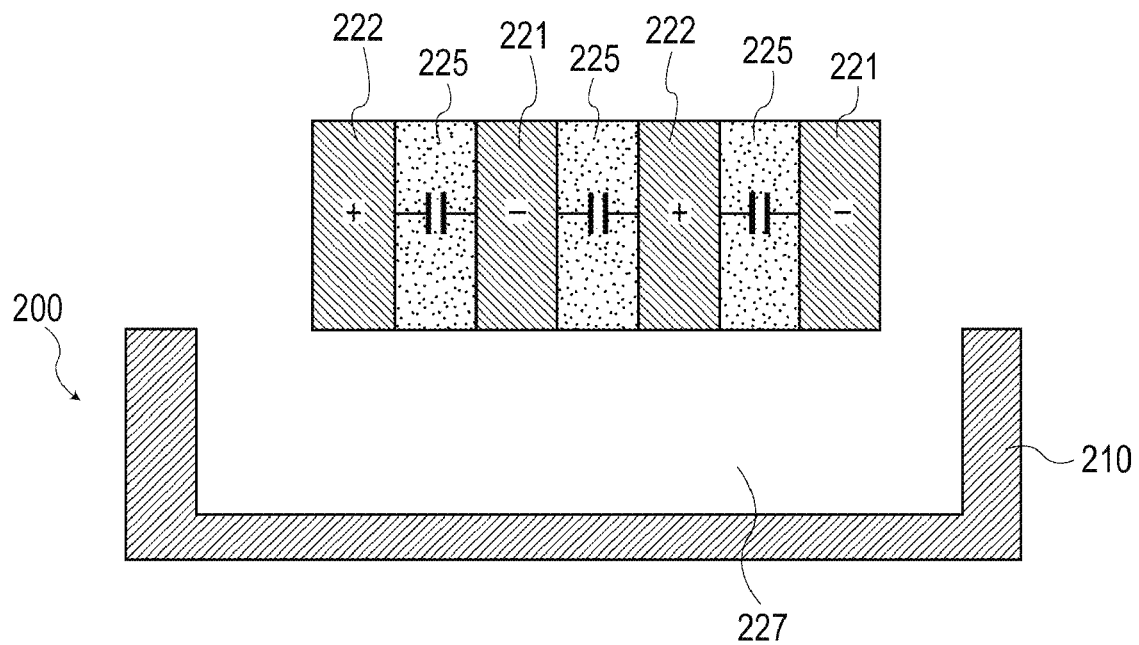
FIG. 5B shows the released structure with those capacitances removed.

Described herein are methods, apparatuses and systems for a chemical sensitive capacitor that has been released from the substrate to eliminate parasitic capacitances. FIG. 5 shows two simple diagrams illustrating this concept. FIG. 5A shows a cross section of an interdigitated electrode capacitor 100, and depicts the substrate 110, conductors 121 and 122 and chemical-sensitive polymer 125. The capacitances that will change upon chemical exposure are through the chemical sensitive layer; however, since the electrodes are resting on the substrate, a large parasitic or shunt capacitance 130, potentially much larger than the chemical sensitive capacitance, will occur through the substrate that the electrodes are sitting on. Since these capacitances are parallel to the capacitor of interest, this results in a degradation of sensitivity. FIG. 5B shows an embodiment of a sensor structure 200, depicting a substrate 210, electrodes 221 and 222, and chemical-sensitive polymer 225, essentially as in FIG. 5A. However, a well is fabricated in the substrate 210, forming an air gap 227 and resulting in loss of parasitic or shunt capacitance (e.g., 130 in FIG. 5A). FIG. 5B shows the effects of removing the substrate. The capacitances through the substrate can be made negligible, since a large air gap 227 now exists between the capacitor and the substrate, leaving only the chemical sensitive capacitor of interest. This structure 200 also allows gas analyte to diffuse into the chemical sensitive polymer 225 from both the top and bottom surfaces, allowing for a faster response.

The systems, apparatuses and devices described herein are fabricated as microfabricated devices (referred to herein as "microdevices" or "microsystems", referring generally to the small size of such systems, devices or apparatuses, and not inferring micrometer-scale or nanometer-scale dimensions). MEMS (microelectromechanical systems) or NEMS (nanoelectromechanical systems), comprising micron- or nanometer-scale mechanical parts/structures) devices are microdevices. Microfabrication methods and compositions useful for preparing the systems, apparatuses and devices described herein are well-known in the MEMS, NEMS, printed-circuit board (PCB) and integrated circuit (IC) manufacturing industries. Microsystems may be manufactured from a variety of materials. Common materials include silicon (e.g. polycrystalline silicon and silicon nitride), glass, carbon (e.g. carbon nanotube and graphene), diamond, polymers and metals. A variety of methods may be used to manufacture the apparatuses (See, e.g., G. Fedder, MEMS Fabrication, in Proceedings of the IEEE International Test Conference (ITC '03), Sep. 30-Oct. 2, 2003, Charlotte, N.C.; H. Baltes, et al., CMOS-MEMS, Wiley-VCH, ISBN 3257310800, January 2005).

The devices described herein can be prepared according to standard MEMS, IC, PCB, etc. design and manufacturing methods and criteria. Electronic circuits can be integrated into the device according to known methods. The devices can be packaged in any suitable manner providing for efficacy of the sensors and overall function of the devices.

Thin films are deposited by any of a variety of methods, for example and without limitation: physical vapor deposition (PVD), such as sputtering and evaporation; and chemical deposition, such as chemical vapor deposition (CVD), including low pressure CVD and plasma enhanced CVD, and thermal oxidation. Exemplary methods for patterning such devices include: mask lithography (photolithography), electron beam lithography, ion beam lithography, X-ray lithography, diamond patterning, injection molding, microstereolithography, silicon surface micromachining, high aspect ratio silicon micromachining and silicon bulk micromachining may be utilized.

Structures may be formed by etching, including wet and dry etching methods. Wet methods include, without limitation: isotropic etching, anisotropic etching, HF etching and electrochemical etching. Dry etching methods include, without limitation: vapor etching, including xenon difluoride etching, plasma etching, including reactive ion etching and deep reactive ion etching (e.g., etching of silicon-on-insulator (SOI) and epitaxial silicon and single crystal reactive etch and metallization (SCREAM) methods). CMOS (complementary metal-oxide-semiconductor) structures/processes may be utilized in conjunction with the MEMS manufacturing methods listed above (see, e.g., G. Fedder, CMOS Based Sensors, in Proceedings of the IEEE Sensors Conference (IEEE Sensors '05), pp. 125-128, Oct. 31-Nov. 3, 2005, Irvine, Calif. and G. K. Fedder, Sensors & Actuators A, vol. 57, no. 2, pp. 103-110, November 1996).

Inkjet printing, for example inkjet printing methods using polymer dissolved in solvent, also can be used to deposit and pattern films (see, e.g., Alfeeli B., et al. Solid State Sensors, Actuators and Microsystems Workshop Hilton Head Island, S.C., Jun. 1-5, 2008, pages 118-121, for inkjet deposition of Tenax TA). Given the significant number of materials, methods and structural/topological variations possible, a person of skill in the field of microfabrication of microdevices (e.g., MEMS, NEMS and IC devices) may use any of a variety of methods and materials to produce/manufacture the microdevices described herein. U.S. Pat. Nos. 6,171,865, 6,850,859, 7,061,061 and 7,338,802, each of which is incorporated herein by reference for its technical disclosure, describe MEMS sensor systems, methods of manufacturing such systems, implementation and use of such systems.

Figure 6A:
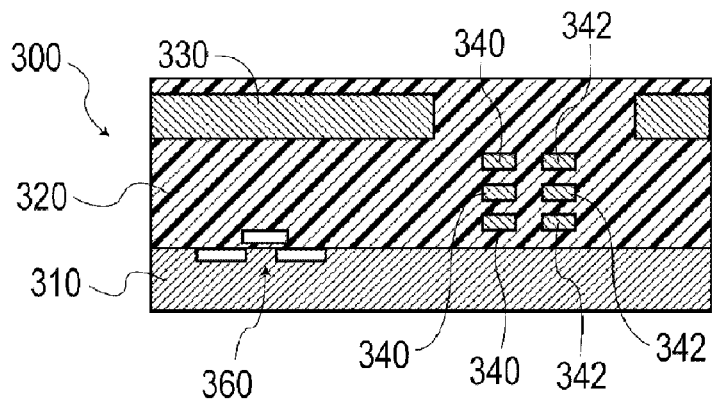
FIG. 6 is a cross section diagram of one possible fabrication process to fabricate one embodiment of the sensor described herein.
Figure 6B:
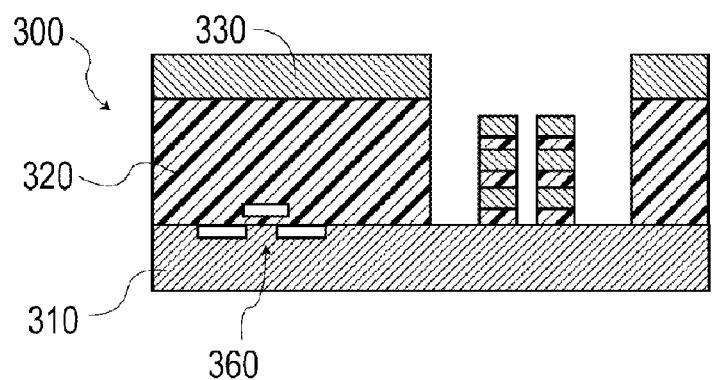
Figure 6C:
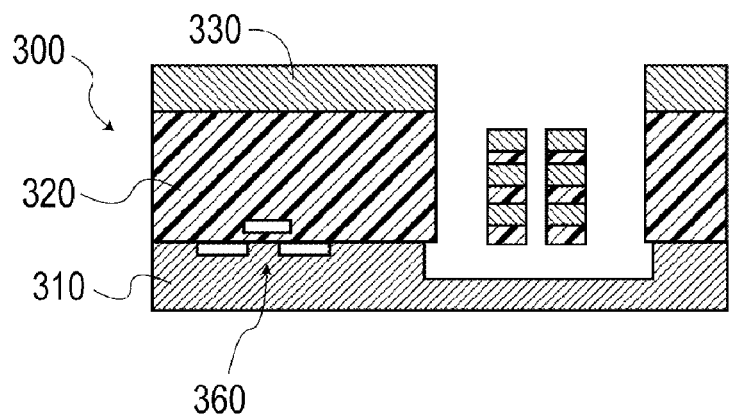
Figure 6D:
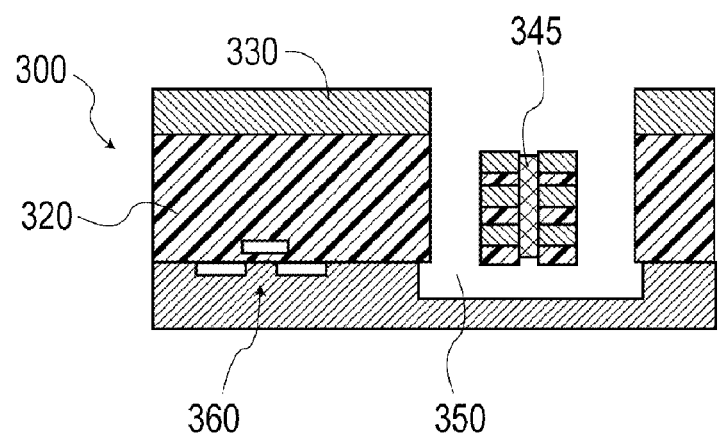

In further detail, the sensors described herein can be fabricated using a number of different fabrication techniques. One technique (G. K. Fedder, et al. Laminated High-Aspect-Ratio Microstructures in a Conventional CMOS Process, in *Proc. of IEEE MEMS* 1996, San Diego, Calif., pp. 13-18, February 1996), shown in FIG. 6, begins with a standard CMOS chip (FIG. 6A). In reference to FIGS. 6A-6D, sensor 300 is depicted, with silicon 310, dielectric 320 (e.g., silicon oxide, silicon dioxide, silicon nitride, silicon oxynitride and doped versions thereof), metal 330, metal electrode 340 and 342 and chemical-sensitive polymer 345 being shown. An anisotropic vertical dielectric etch (FIG. 6B) is followed by a timed directional (anisotropic) silicon etch and a timed isotropic silicon etch to release the MEMS structure (FIG. 6C). Sensitive polymer 345 can be added by using a custom drop-on-demand inkjet system (L. Weiss, et al. Inkjet deposition system with computer vision-based calibration for targeting accuracy, Technical report CMU-RI-TR-06-15, Carnegie Mellon University, March, 2006) to deposit the polymer in solution. Final product is shown in FIG. 6D, depicting air-gap 350, as well as CMOS circuitry 360 for illustration. As would be appreciated by those of ordinary skill in the art of CMOS fabrication techniques and, more generally, semiconductor structure fabrication techniques, the four steps depicted in FIGS. 6A-6B may include additional steps, and further, identical and substantially or essentially identical structures may be fabricated by a variety of methods, which would become apparent in light of the teachings of this disclosure.

Figure 7A:
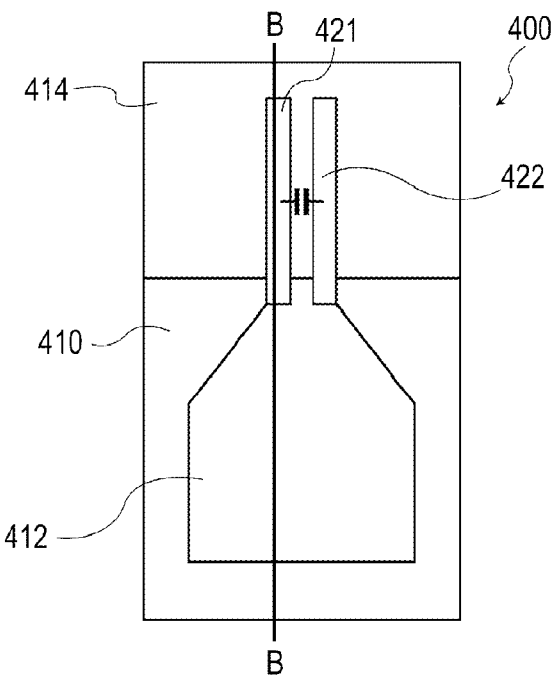
FIGS. 7A and 7C are top view schematic diagrams of a single channel device with inkjet well before (FIG. 7A) and after (FIG. 7C) deposition of the chemical sensitive material.
Figure 7B:
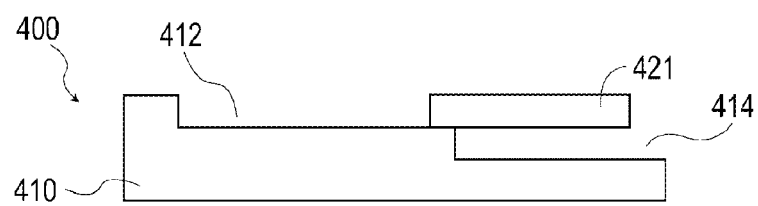
FIG. 7B is a side view of the device of FIG. 7A at cut line B.
Figure 7C:
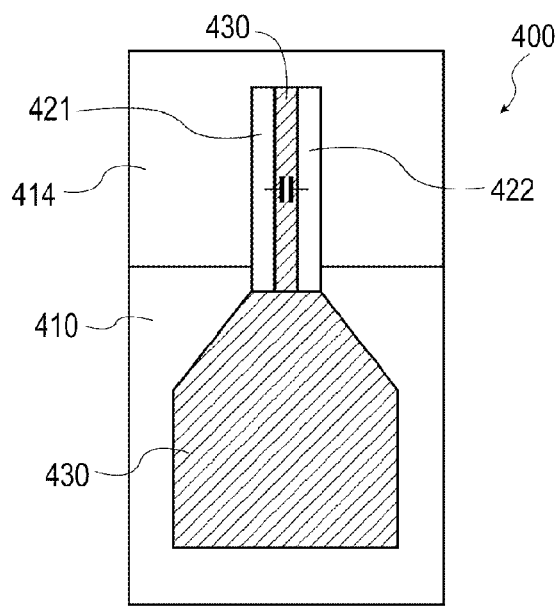

Chemical sensitive material can be added through a number of different methods. One embodiment uses a capillary wicking technique to avoid jetting directly on a fragile released structure. Sensitive material in solution is ink-jetted into an anchored well attached to the structure; capillary forces then pull the solution into the released structure, filling it with sensitive material. FIGS. 7A and 7C shows a top view of the structure before (7A) and after (7C) inkjet deposition of polymer. FIG. 7B shows a side-view of the structure of FIG. 7A at cut line B. In FIGS. 7A-7C, the sensor structure 400 comprises a substrate 410 having an inkjet well 412 and an etched area 414 below cantilevered electrodes 421 and 422. In FIG. 7C, chemical-sensitive polymer 430 is shown. Only one capillary channel is shown in FIGS. 7A-7C, however a multiplicity of parallel channels can be used as illustrated in the cross-section of FIG. 5B where three parallel channels are shown.

A large number of polymers, including polyimide, polymethyl methacrylate (PMMA), poly(ethylene teraphthalate) (PET), polysulfone (PSF), cellulose acetate butyrate (CAB), polyethynyl fluorenol (PEFI), have been used for humidity application. Polymers may be selected for their ability to selectively form weak reversible chemical interactions (hydrogen bonds, van der Waals bonds, and dipole—dipole interactions) with a particular analyte. Liquid polymers or polymers with a low modulus of elasticity may be preferred in certain instances because they absorb analytes more quickly than rigid polymers (S. V. Patel et al. Chemicapacitive microsensors for volatile organic compound detection Sensors and Actuators B 96 (2003) 541-553). Polymers may be chosen based on the findings in the literature applying solubility parameters. Other factors in choosing the polymers include stability, ease of acquisition, solubility in a suitable solvent and ease of coating application (S. V. Patel et al. *Sensors and Actuators B* 96 (2003) 541-553).

As an example, the fluoroalcohol SXFA has an affinity for hydrogen-bonding bases and is useful for the detection of chemical warfare agents, such as Sarin. Dicyanoallyl silicone (e.g., OV-275, 20,000 cSt) and cyanopropyl methyl phenylmethyl silicone (e.g., OV-225, 9,000 cSt), are siloxane-based compositions that can be used to detect byproducts and impurities found in explosives. Polyethylene-co-vinylacetate (PEVA, e.g., 40% acetate content), polyepichlorohydrin (PECH, e.g., 700,000 MW), polycarbonate urethane (PCUT), polyisobutylene (PIB, e.g., 1350 MW), and polydimethyl siloxane (PDMS, e.g., 100,000 cSt (centistokes)) may be used to detect volatile organic compounds (VOCs) with moderate to low polarity values (S. V. Patel et al. Sensors and Actuators B 96 (2003) 541-553). Other useful polymeric materials include, poly(dimethyl siloxane (PDMS) and poly(etherurethane) (PEUT).

Nanocomposites, such as nanocluster and nanocrystalline materials, also are useful as chemical-sensitive dielectric materials in the capacitor devices described herein. Nanocomposites contain nanometer-sized (e.g. 1-100 nm in at least one dimension) particles of any suitable morphology, such as metallic or ceramic particles. Examples of suitable nanocluster materials include, without limitation, silicon nanoclusters, metal nanoclusters and gold nanoclusters. Nanoclusters and nanoparticles can be capped with a variety of thiol groups, for example that contain alkane, alkene or other carbon containing moiety. In one example, Wei Yao, et al. disclose a Gold-PVA nanocomposite that is useful for moisture sensing. (A capacitive humidity sensor based on gold-PVA core-shell nanocomposites Sensors and Actuators B 145 (2010) 327-333). In another example, silica nanoparticle compositions, such as mesoporous silica (e.g. 2-50 nm pore diameter) or aerogels, have found use as chemical-sensitive dielectric materials in capacitance sensors for detecting humidity and VOCs. An aerogel is a mesoporous ceramic material. Silica in the form of aerogel has a highly porous structure mainly consisting of mesopores supported by a nanoparticle cross-linking framework (Chien-Tsung Wang et al. Humidity sensors based on silica nanoparticle aerogel thin films Sensors and Actuators B 107 (2005) 402-410).

Figure 8:
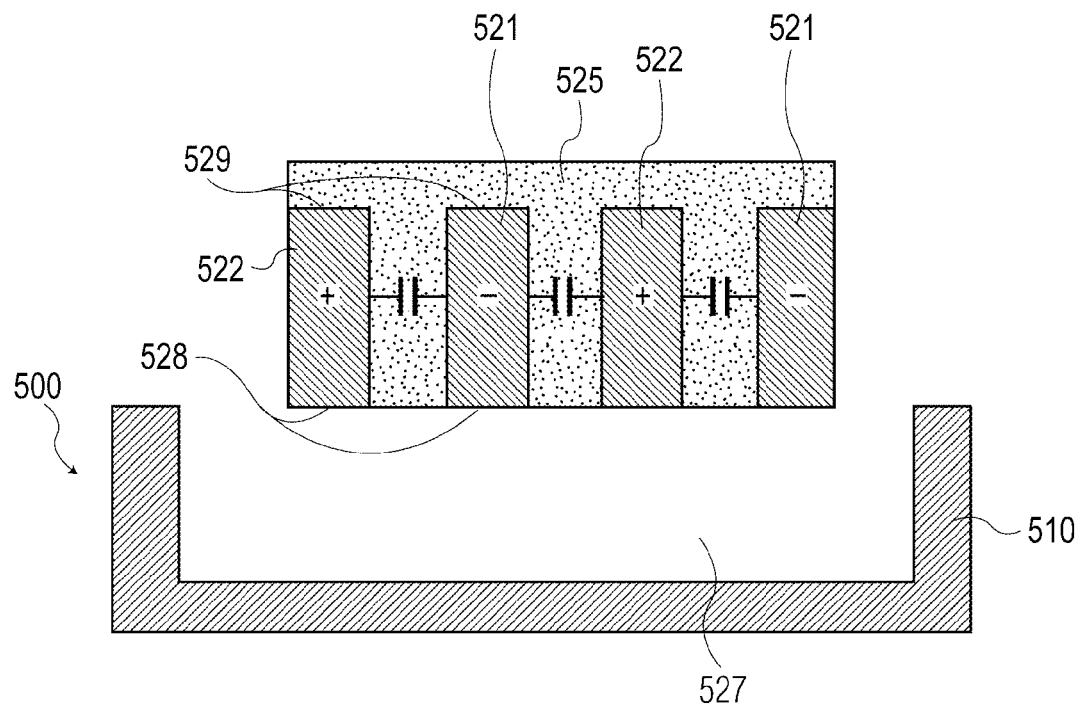
FIG. 8 is a cross section diagram of a capacitive structure coated by jetting directly on the structure.

A second embodiment of the present invention consists of inkjetting directly on a released structure, coating the structure, resulting in the structure shown in FIG. 8, since capillary forces will pull material in between the capacitor beams. FIG. 8 shows an embodiment of a sensor structure 500, depicting a substrate 510, electrodes 521 and 522, chemical-sensitive polymer 525 and air-gap 527. Inward-facing sides 528 and outward-facing sides 529 of electrodes 521 and 522 are shown. This structure eliminates the need for an inkjet well, reducing the necessary die area. By coating the top surface, the parallel capacitance through the air above the structure is also reduced, increasing the sensitivity of the device. The material may also coat the bottom of the structure, though that particular version is not shown in FIG. 8.

Figure 9:
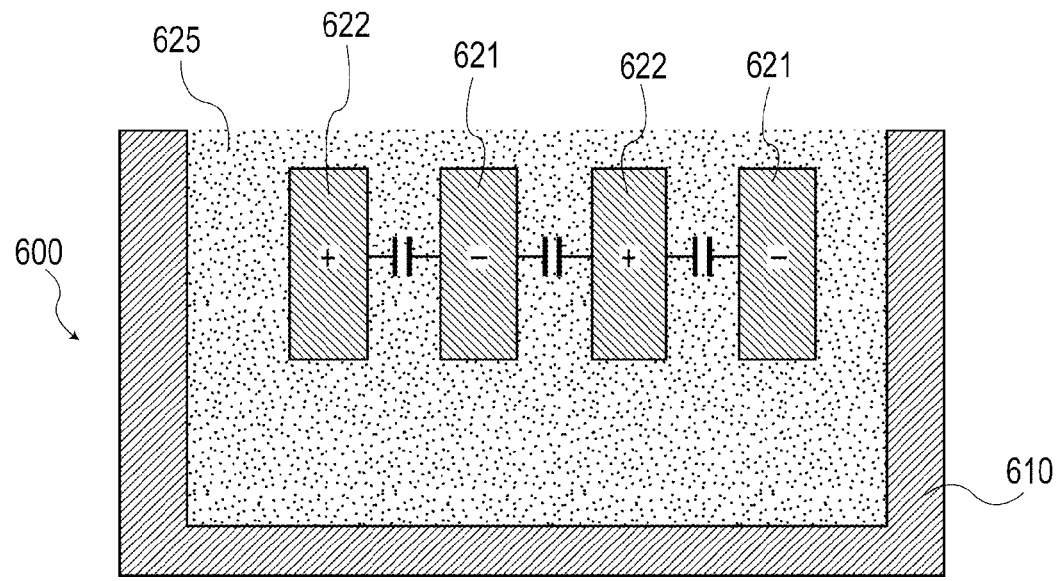
FIG. 9 is a cross section diagram of a capacitive structure encased in chemical sensitive material.

A third embodiment consists of completely encasing the structure with polymer, as shown in FIG. 9. This could be done by completely filling up the release cavity with sensitive material. In reference to FIG. 9, sensor structure 600 includes a substrate 610, electrodes 621 and 622, chemical-sensitive polymer 625, but no air-gap.

Figure 10:
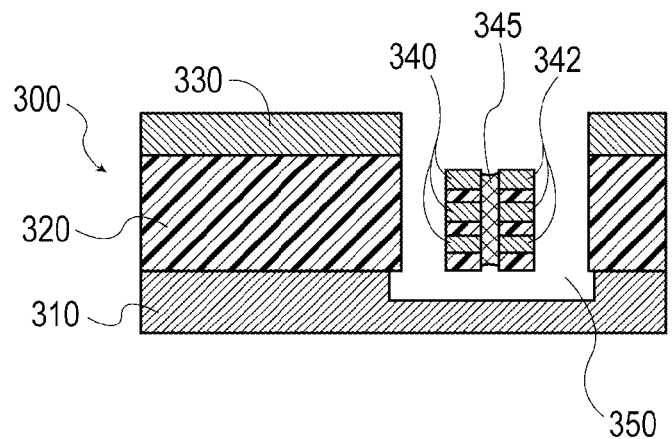
FIG. 10 is a cross section diagram of a of a capacitive structure made using a CMOS process with inkjetted chemically sensitive material.

A more specific implementation of the device can be made directly in a CMOS process by stacking CMOS metal layers and then anisotropically etching the surrounding dielectric and underlying silicon to make microstructures. This CMOS microelectromechanical process is described in Fedder, et al. (Laminated High-Aspect-Ratio Microstructures in a Conventional CMOS Process", in *Proc. of IEEE MEMS* 1996, San Diego, Calif., pp. 13-18, February 1996) and in U.S. Pat. No. 5,970,315. FIG. 10 shows a version of the structure in FIG. 5D with three CMOS metal layers stacked to form the suspended beams and electrodes 340 and 342. Of particular note, the depth of the air gap is not to scale in this figure. The air-gap 350 would normally be much larger (about 10 times larger than the height of dielectric 320). Reference numbers are the same as in FIG. 5D. The metal layers 340 and 342 (the electrodes/conductors) on each beam can be interconnected with vias. The capacitance is then detected between these two sets of metal-layer electrodes. Functionally, this version operates as in FIG. 5B, however it is more easily fabricated directly in a CMOS MEMS process.

This device can be used with a variety of gas chemical analytes based on the choice of sensitive material deposited. One possible embodiment would be a humidity sensor, in which the sensor would be used to detect water vapor. Other possible analytes include (but are not limited to) various volatile organic compounds. One possible sensing material is polyimide, which is primarily used for humidity sensing. As described above, numerous other polymers have been used in capacitive sensors to detect other analytes. Patel et al. (*Sensors and Actuators B* 96 (2003) 541-553) gives a few possibilities of sensitized polymers, such as polydimethyl siloxane (PDMS) and polyisobutylene (PIB), and U.S. Pat. No. 5,970,315, incorporated herein by reference for its technical disclosure, also provides a list of some analytes that these polymers are sensitive to. Liquid polymers, nanoclusters, nanocomposites, aerogels and sol-gels are other possible chemically sensitive materials that can be incorporated into the device.

Figure 11:
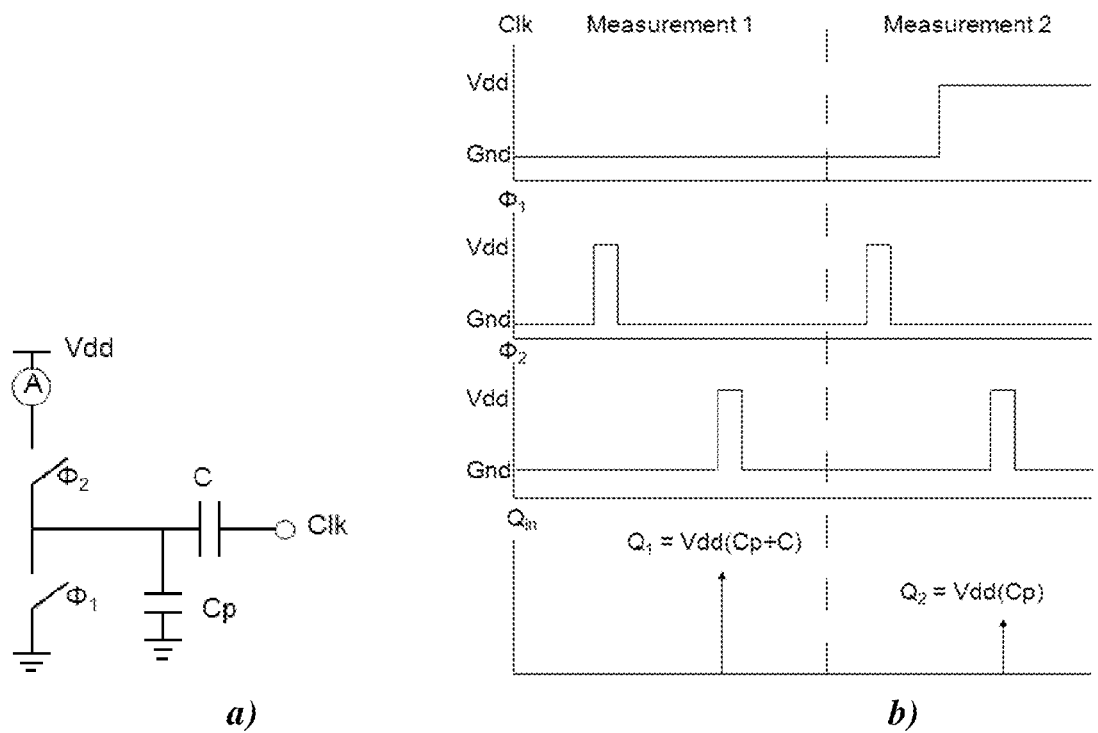
FIG. 11 illustrates (a) a charge-based capacitance measurement circuit and (b) a timing diagram for a sensor as described herein.
Figure 12:
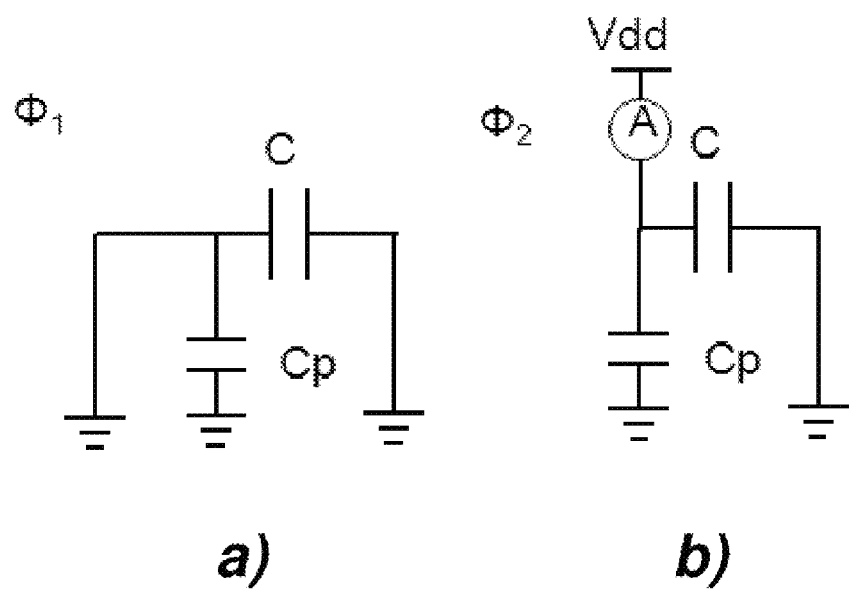
FIG. 12 illustrates measurement Cycle 1 (Clk input connected to ground) during clock phase $\Phi_1$ (a) and $\Phi_2$ (b) for a sensor as described herein.
Figure 13:
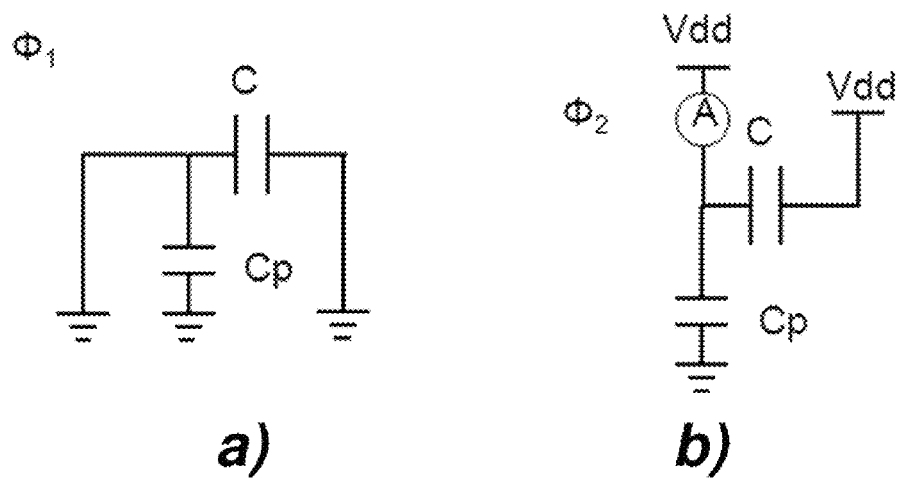
FIG. 13 illustrates measurement Cycle 2 during clock phase $\Phi_1$ (a) and $\Phi_2$ (b); Clk input is connected to ground during phase $\Phi_1$, and connected to Vdd during phase $\Phi_2$ for a sensor as described herein.

The chemical sensitive capacitor, once filled, can be detected with any electronics designed for detecting capacitance change. One possible technique, charge-based capacitive measurement (CBCM) (Y. Chang, Y., et al. Charge-Based Capacitance Measurement for Bias-Dependent Capacitance, IEEE Electron Device Letters, Vol. 27, No. 5, May 2006, pp. 390-392), is illustrated in FIG. 11. FIG. 11a) shows a schematic of the testing circuit, which consists of two switches, one connected to Vdd and one connected to ground. C is the chemical sensitive capacitor, Cp is a parasitic capacitance to ground. FIG. 11b) shows a timing diagram of the testing circuit. $\Phi_1$ and $\Phi_2$ are non-overlapping clocks, as shown. A measurement is first taken with Clk set to 0 V. The equivalent circuits in the two clock phases are shown in FIG. 12. During $\Phi_1$, both capacitances are discharged to 0 V. During $\Phi_2$, both capacitors are charged up through an ammeter, giving the charge necessary to charge both the capacitors to $V_{dd}$. During the second measurement, Clk is grounded during $\Phi_1$, and set to $V_{dd}$ during $\Phi_2$. The equivalent circuits during the two clock phases are shown in FIG. 13. During $\Phi_1$, both capacitances are again discharged to 0 V. During $\Phi_2$, only $C_p$ is charged up, because no voltage drop occurs across the sensing capacitance; this allows the parasitic capacitance to be isolated and subtracted away. Switched capacitor circuits and capacitive integration circuits are two other example approaches to measure capacitance. Many other circuit designs to measure capacitance are available in the literature and well known.

Figure 14:
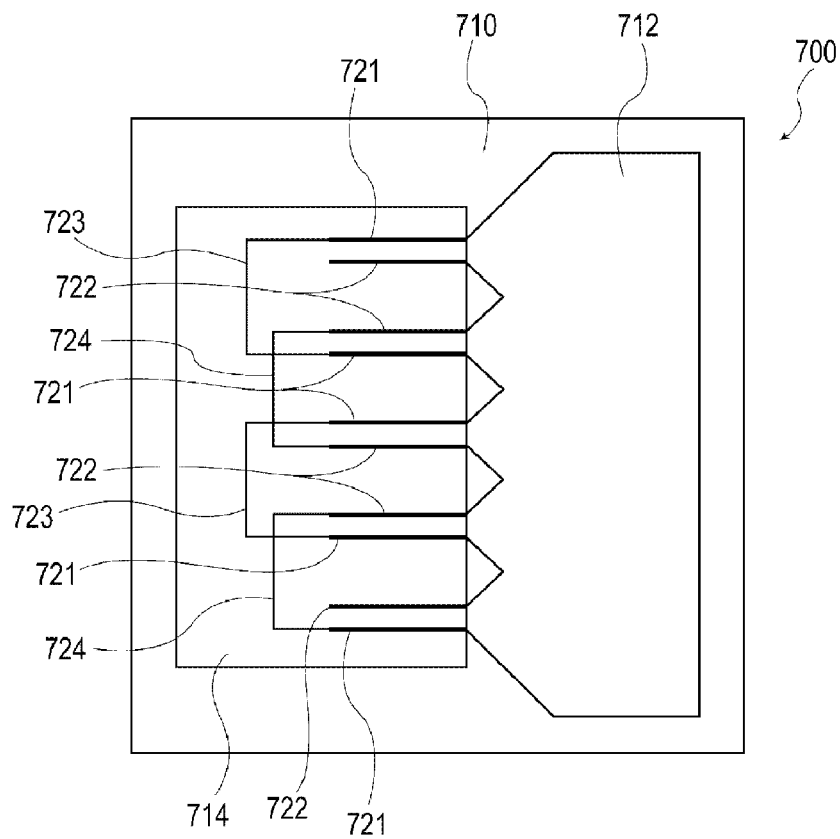
FIG. 14 is a top view diagram of a 5 channel wicked humidity sensor.

A device consisting of five parallel wicking channels, shown in FIG. 14, was fabricated by CMOS processes and was used to test the humidity response. Sensor 700 comprises substrate 710 and includes inkwell 712 and etched well 714. Five electrode pairs including electrodes 721 and 722 are depicted. Electrodes 721 are connected by conductors 723 and electrodes 722 are connected by conductors 724. The device is made in a CMOS MEMS process so that the conductors 723 and 724 are located on different metal levels in the structure and therefore do not short-circuit. The larger sensing capacitance was more easily resolved from the fixed parasitic capacitance to ground, allowing for more accurate measurements.

Figure 15:
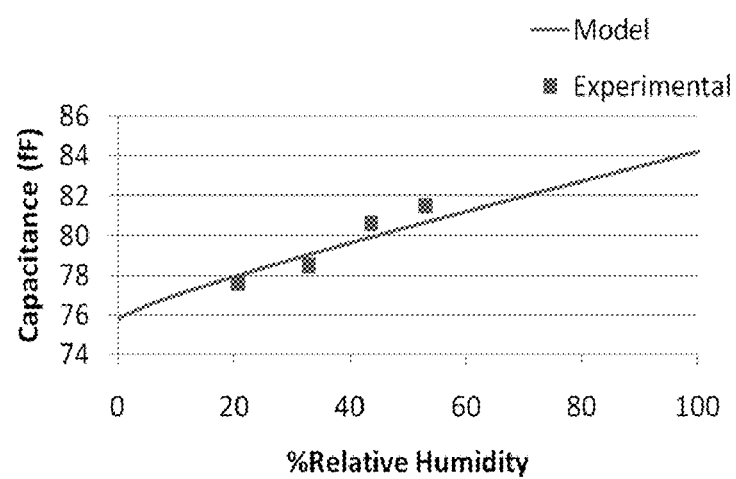
FIG. 15 illustrates humidity test response for the 5 channel wicked humidity sensor.

The capacitance of the sensor was measured for a range of humidity values and compared to a theoretical model (FIG. 15). The sensitivity is 0.16% change in capacitance for every 1% change in humidity.

Figure 16A:
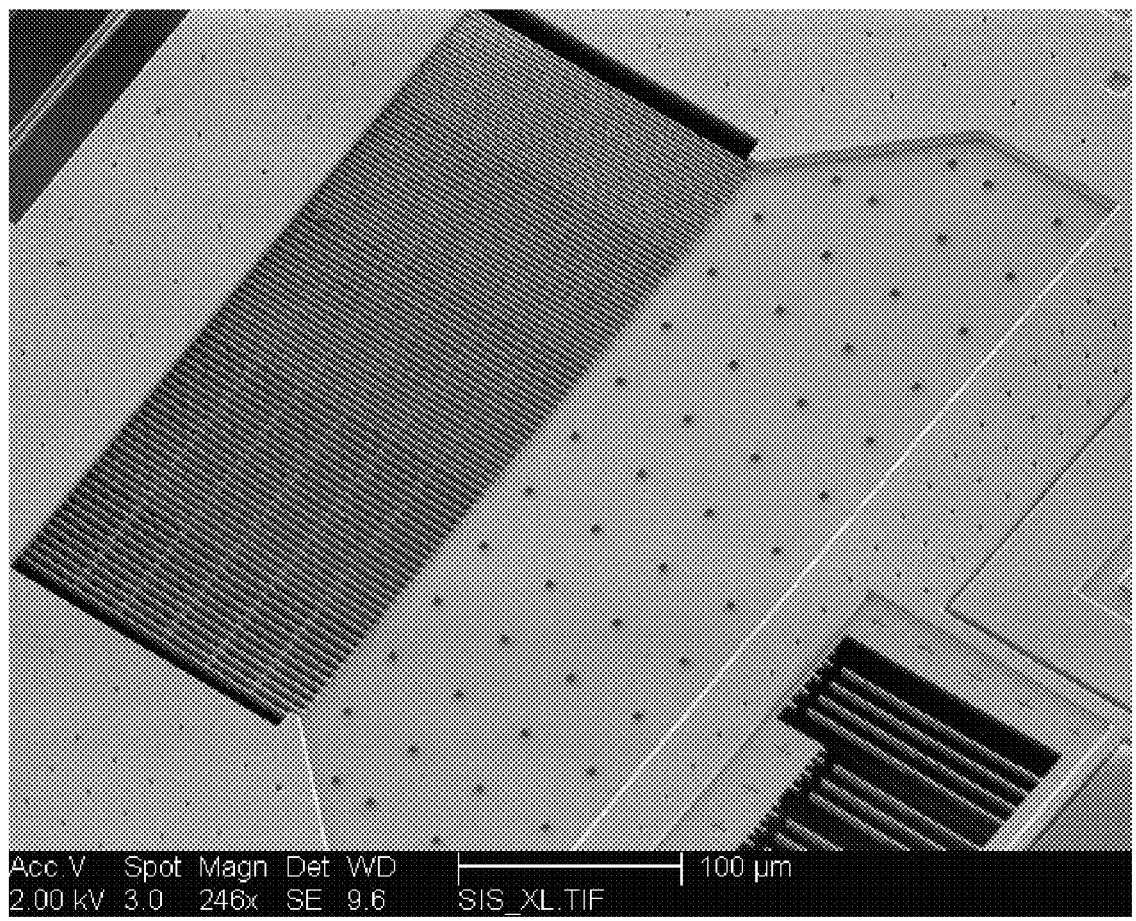
FIG. 16A is a photomicrograph of an 87 channel coated humidity sensor.
Figure 16B:
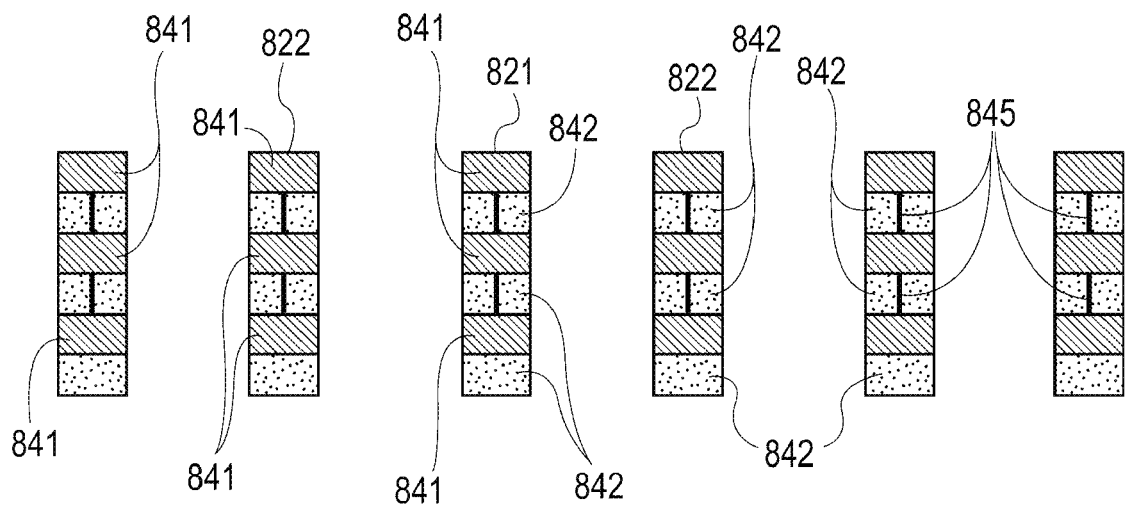
FIG. 16B is a schematic diagram showing details of the capacitor beam and truss assembly of the device depicted in FIG. 16A at a cross section that does not include a truss.
Figure 16C:
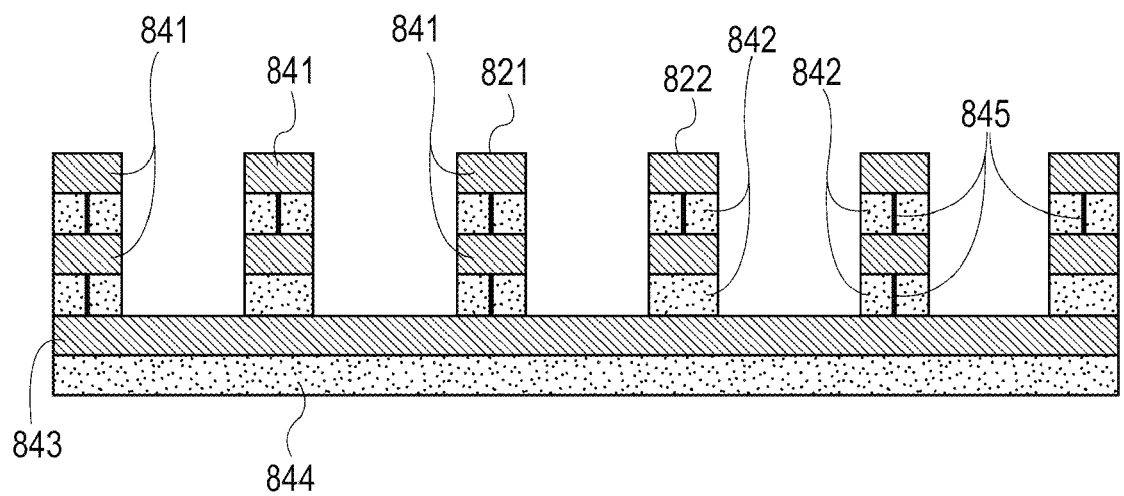
FIG. 16C is a schematic diagram showing details of the capacitor beam and truss assembly of the device depicted in FIG. 16A at a cross section that includes a truss.
Figure 17:
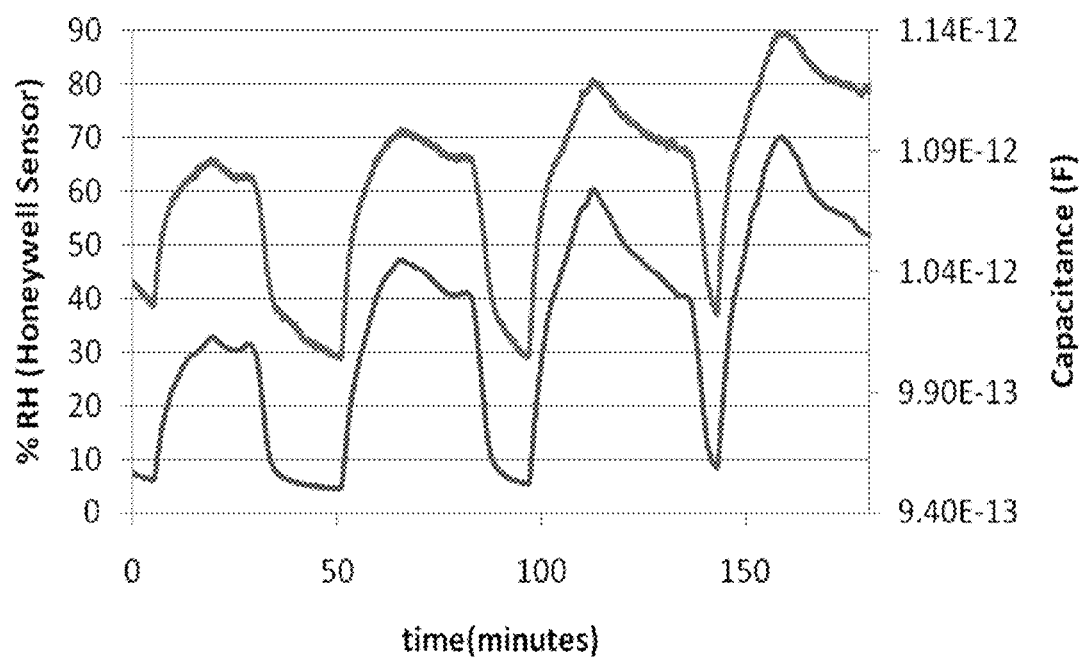
FIG. 17 illustrates a humidity test with the 87 channel humidity sensor (top trace) as compared to a reference sensor (bottom trace).

A larger device created by inkjetting directly on the beams (a photomicrograph of the structure before inkjetting is shown in FIG. 16A) was also fabricated and tested. The fragile cantilever beams, such as those shown in FIG. 14, are impractical for a coated device due to the damage caused by ink-jet drops deposited directly onto the structure. The wicking channels in FIG. 16A are fixed to the substrate at both ends, and trusses are used to connect the beams every 20 μm, giving the mechanical stability necessary to survive an inkjet drop. FIG. 16B is a cross section of six of the 87 beams of FIG. 16A at the large portions of the structure where the supporting truss does not exist. FIG. 16C is a cross section of six of the 87 beams of FIG. 16A at the small portions of the structure where the supporting truss exists. For FIGS. 16B and 16C, electrodes 821 and 822 are shown, and the multi-layered structures of metal 841 and silicon dioxide 842 are depicted. In FIG. 16C, a metal 843 and metal oxide 844 truss is shown extending between electrodes 821 and 822. Vias 845 are depicted in both FIGS. 16B and 16C, and of note, the truss of FIG. 16C is only electrically-connected to the metal layers 841 of electrodes 821, and not to the metal layers of electrodes 822, preventing shunting. While some parasitic capacitance is created by the use of the truss structure, it is negligible. After inkjetting, the measured capacitance of the structure was 1.1 pF. FIG. 17 shows a plot of the sensor output as the humidity concentration is pulsed to different values.

Figure 18:
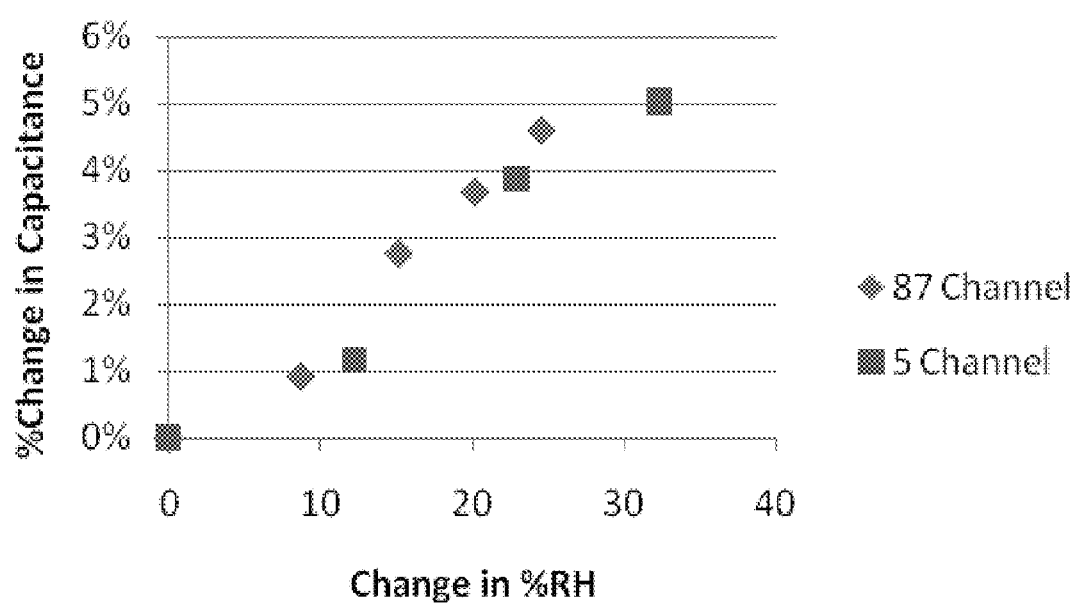
FIG. 18 illustrates humidity tests for both the 5 channel and the 87 channel capacitive humidity sensors.

FIG. 18 shows a plot of the response to changes in relative humidity for both the five channel and the 87 channel capacitive sensors. The measured sensitivity of the 87 channel device was 0.18% change in capacitance for every 1% change in relative humidity.

Figure 19:
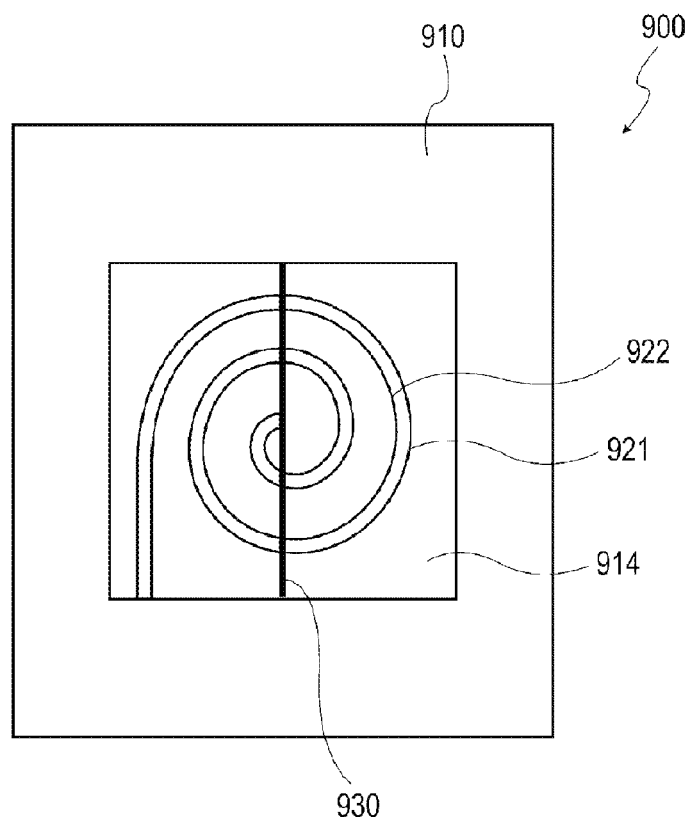
FIG. 19 is a schematic diagram of a geometric variation of the sensor described below.

As would be evident to those of ordinary skill in the art, alternate geometries may be used to accomplish the same structural and functional goals. For example, the conductors/electrodes do not have to be linear, but can be fabricated in angled or curved structures, such as concentric squares, circles or other polygons, spirals, or other topologies. FIG. 19 shows a simplified and non-limiting example of a sensor spiral structure 900 comprising a substrate 910 having a well 914. Spiral electrodes 921 and 922 are shown, and chemical-sensitive polymer between electrodes 921 and 922 is omitted for clarity. A support 930 is fabricated into the structure, and suitable electrical conductors can be integrated into the support 930. The number of turns in the spiral structure is limited only by the overall size of the sensor and the fabrication techniques. In the spiral structure depicted in FIG. 19, the outer electrode 921 would be longer than the inner electrode 922. The electrodes may cross from inner-to-outer at one or more points, so that the overall length of the electrodes 921 and 922 are equal, though it would be preferable not to have the same charge electrode adjacent to each other. Alternately, the distance between electrodes 921 and 922 may be equal, including spacing between separate "turns" of the electrode pair, yielding multiple electrode pairs, as illustrated in the "beam" embodiment depicted in FIG. 16B.

The sensors described herein can be used for any environmental testing, so long as the capacitance of the sensor changes over time with exposure to an environmental condition, such as humidity, temperature, chemicals, $CO_2$, etc. The device may be used to sense chemical(s) within a mask, such as a breathing mask, a gas mask or a respirator.

The devices described herein can be prepared according to standard MEMS, IC, PCB, etc. design and manufacturing methods and criteria. Electronic circuits can be integrated into the device according to known methods. The devices can be packaged in any suitable manner providing for efficacy of the sensors and overall function of the devices. As should be recognized by those of ordinary skill in the art, considerable variation in the layout and components of such a device would result in equivalent functionality.

Figure 20:
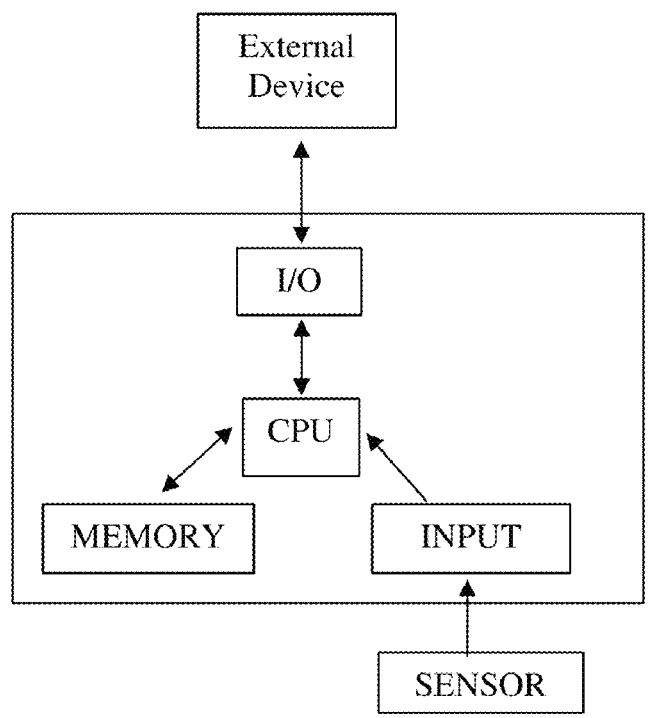
FIG. 20 is a schematic diagram of a computer system useful in implementing the sensor devices and methods described herein.

FIG. 20 illustrates one embodiment of a computer system for use in implementing the sensor described above. The capacitive sensors described herein will comprise sufficient electronic circuitry to permit its intended use. At a minimum, and in reference to FIG. 20, electric leads are connected to the capacitor structures and to an "INPUT" of a sensor computing device. The "INPUT" of sensor computing device may comprise one or both of an amplifier (e.g., operational amplifier, preamplifier, differential amplifier, etc.) to amplify signal from the sensors and an analog-to-digital chip/circuit to convert raw analog data obtained from sensors to a digital format. Signal received from sensors is optionally converted to a digital signal, but conversion to a digital signal may be preferred in certain embodiments.

The "CONTROL" of sensor computing device comprises computer software ("software" (or computer software) includes, without limitation: application software, middleware, computer processes, programming languages, code, system software, operating systems, testware, firmware, device drivers, programming tools, data, etc. for carrying out a specific task) and/or computer hardware. Useful computer software and/or hardware constituents are readily developed by those of ordinary skill in the related arts, such as using assembly language on a microcontroller, or using any of a large variety of available programming resources, languages, for example and without limitation: C, Matlab and Java.

The sensor computing device comprises a central processing unit ("CPU") and "MEMORY" which stores data collected and any useful computer software (e.g. firmware) for obtaining, converting, analyzing, storing and uploading data. Memory may comprise of any useful data storage device, including ROM, PROM, FPROM, OTP NVM, RAM, EEPROM, flash memory, etc. Because the device in many instances is miniaturized, the memory component is, to the extent possible, miniaturized. The CPU can comprise of any useful processing circuitry, chip (microprocessor)/hardware/software, combinations etc. The sensor computing device also typically comprises an input/output interface ("I/O" or communications interface), such as a wired interface such as a such as a USB (e.g., USB 2.0), Ethernet, serial (e.g. RS232), GPIB (General Purpose Interface Bus, e.g. IEEE-488), or firewire interface, or a wireless interface, such as an IEEE 802.11 (e.g., 802.11(a), 802.11(b), 802.11(g) or 802.11(n) interface), a Bluetooth interface or an RFID-based interface for communicating with an external device, which can be a second computing device (e.g., PC, laptop, smartphone, PDA, tablet PC, iPad, etc.) for uploading data, analyzing data, outputting data, downloading firmware to the device, or for any activity. Device can be powered by batteries, such as rechargeable batteries (e.g., via a USB interface) or any suitable power source.

The sensors described herein are suitable for use in a remote sensor, such as for monitoring analyte levels in a gas mask or filtration device to determine the presence of environmental contamination, the status of adsorbent levels in the mask (indicating breakthrough of, e.g., VOCs), or to monitor a subject's respiration. As such, the miniaturized device can be installed in a gas mask, and analyte levels can be monitored in the manner indicated and the results stored within the system memory. Periodically or continually the data can be uploaded to an external computing device for monitoring, analysis, storage, etc.

Signal received from sensors is optionally converted to a digital signal, but conversion to a digital signal may be preferred in certain embodiments. In certain embodiments, the signal from sensor is compared to stored data by differencing the output of the sensor either by analog or digital processing. Where data is obtained remotely and transferred to a second computer, the differencing or other comparison methods can be performed either at the sensor computing device or external device. It may in many instances be in such a configuration to conduct the differencing at the sensor computing device, though if a real-time connection (typically wireless, including substantially real-time connection, meaning that data is transferred from the sensor device to the external device regularly, such as every second, 10 seconds, minute or even hourly or daily depending on system tolerances) between the sensor and external device is used, differencing and comparison against reference data, if used, can be conducted in one or both of the sensor and external devices in a stand-alone or distributed manner. Alarm functions, indicative of analyte levels reaching a desired threshold, may be programmed or otherwise incorporated into the devices described herein to provide a discernable signal indicating crossing of a threshold. One non-limiting example of such a threshold is an increase in analyte concentrations in a gas sample indicative of VOC breakthrough in a gas mask indicative of loss of function of an adsorbent material in the gas mask.

Figure 21A:
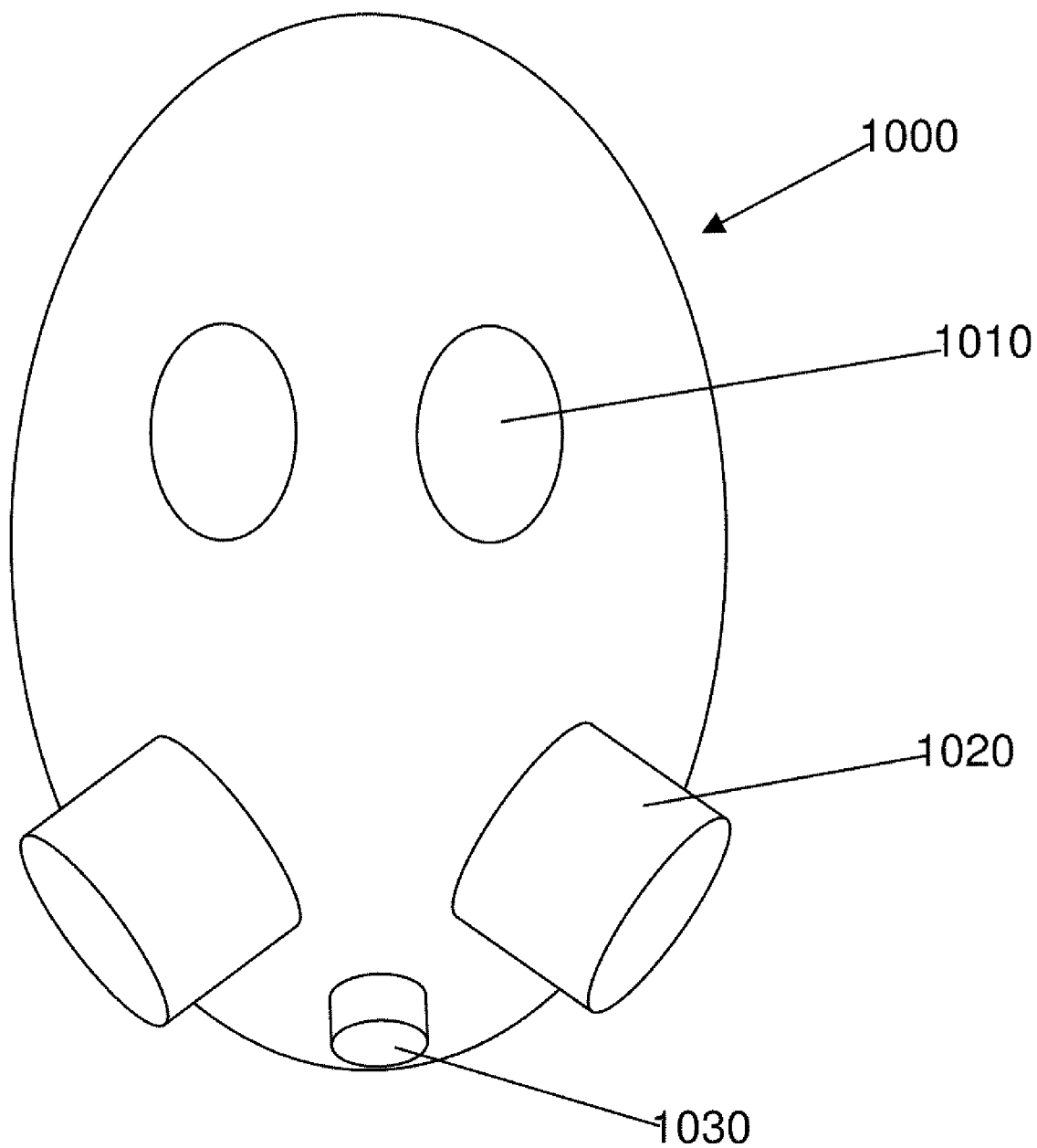
FIGS. 21A and 21B are schematic diagrams of two alternate embodiments of a gas mask comprising a sensor as described herein.
Figure 21B:
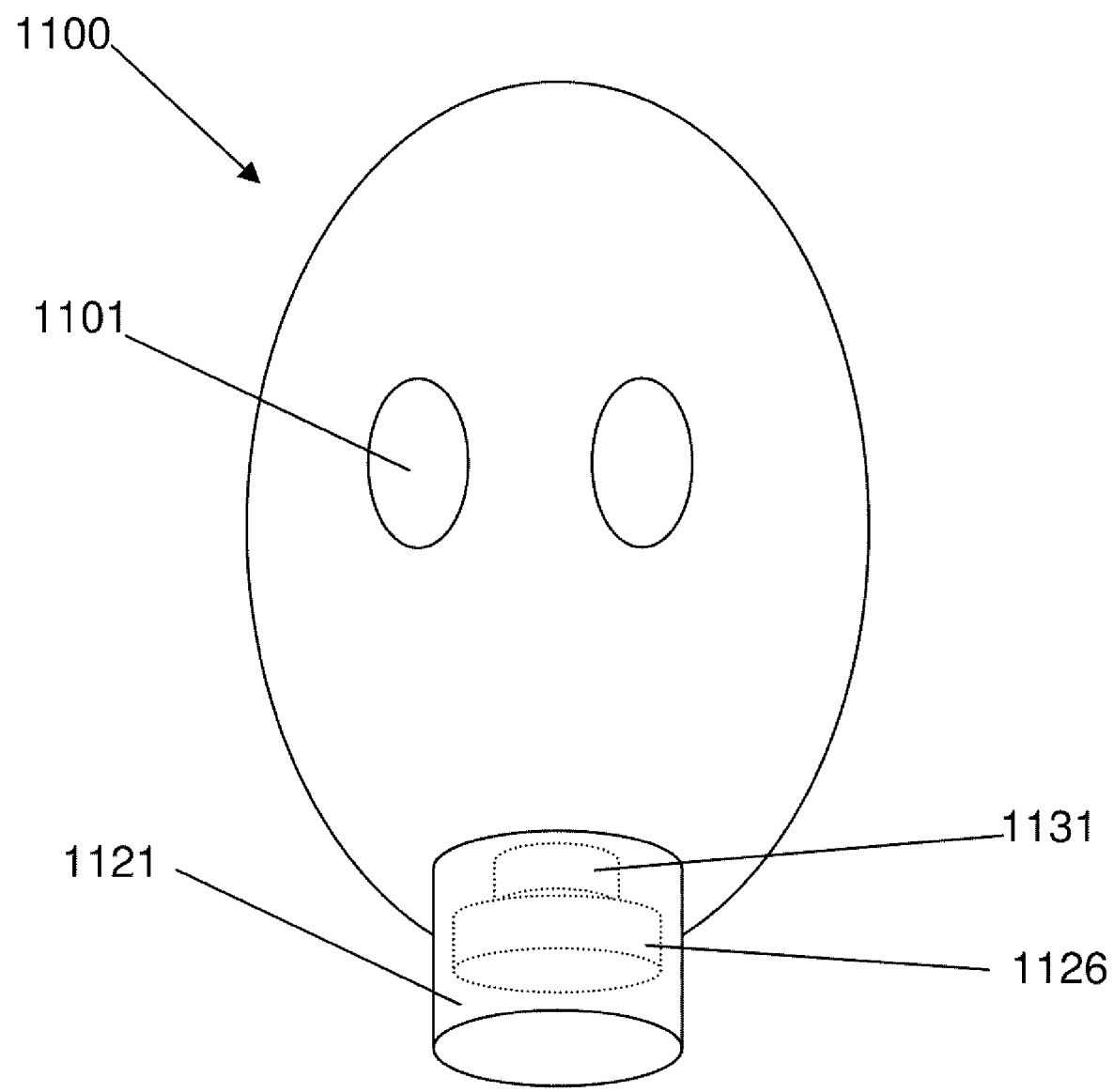

FIGS. 21A, 21B, 22A and 22B are simplified schematic diagrams of gas mask/respirator structures comprising a sensor device as described herein. FIG. 21A illustrates a gas mask 1000 showing transparent eye windows 1010, filtration canisters or cartridges 1020 and sensor device 1030. Pressure differentials from inhaling and exhaling can cause air/gas to pass through the sensor device 1030. As described above, the sensor device may comprise on-board computer and communications functions. Given the ability to micro-manufacture the device, e.g., with MEMS and/or NEMS processes, the device may be quite small in relation to the size of the mask. Alternately, as shown in FIG. 21B, the sensor device may be placed inside the mask, for instance within the canister structures 1020 so that air passing through the canisters also pass through the mask 1100, comprising eye windows 1101 and a single canister 1121, comprises within the canister 1121 a filtration media canister 1126 and sensor device 1131. This in-line configuration is particularly useful for sensing analyte (e.g., VOC) breakthrough indicative of failure or imminent failure of the filtration media.

Figure 1:
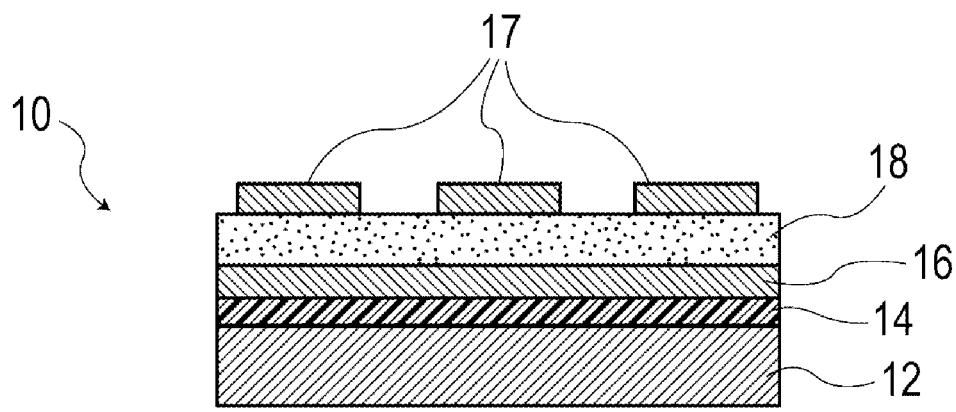
FIG. 1 is a cross section diagram of a prior art vertical parallel plate capacitive sensor.
Figure 2:
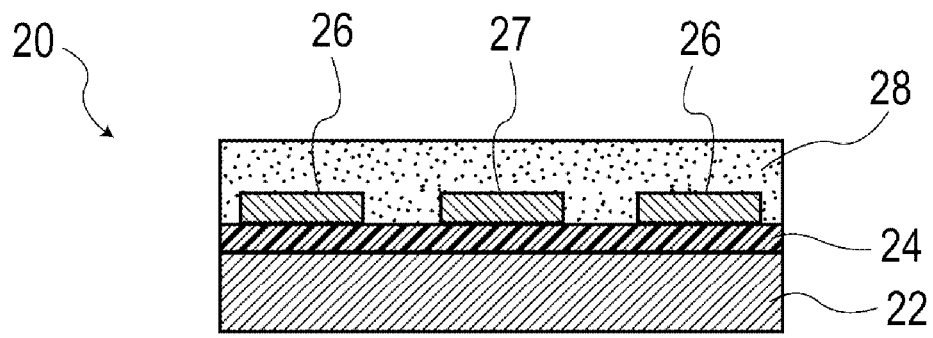
FIG. 2 is a cross section diagram of a prior art coated interdigitated electrode capacitive sensor.
Figure 3:
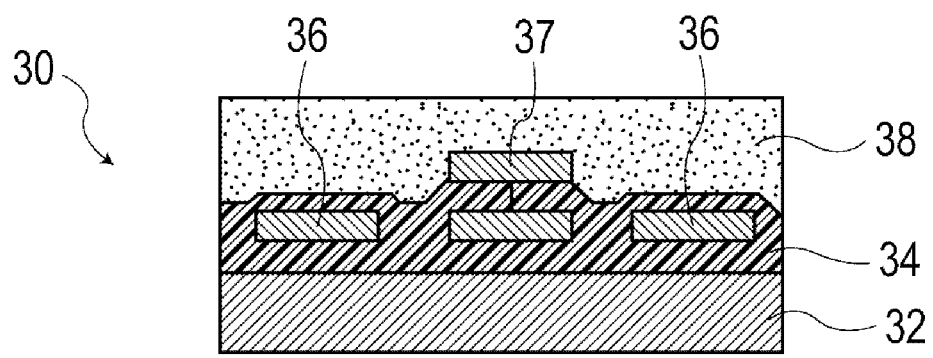
FIG. 3 is a cross section diagram of a simplified model of the prior art ETH Zurich integrated capacitive sensor.
Figure 4:
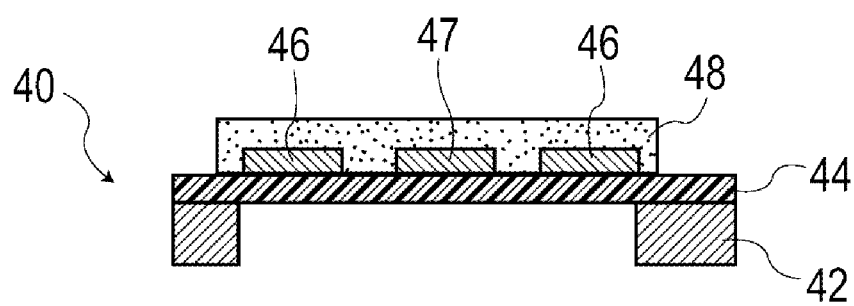
FIG. 4 is a cross section diagram of a prior art capacitor with substrate removed.
Figure 22A:
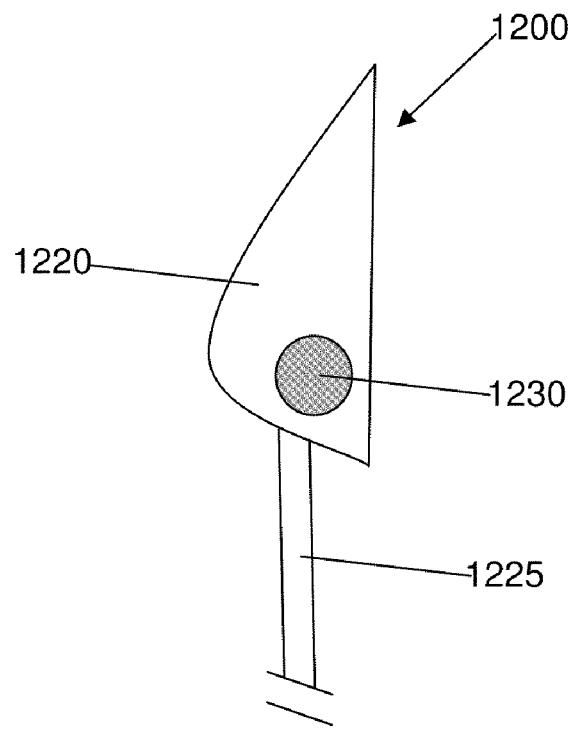
FIGS. 22A and 22B are schematic diagrams of alternate embodiments of a respirator mask comprising an embodiment of a sensor as described herein.
Figure 22B:
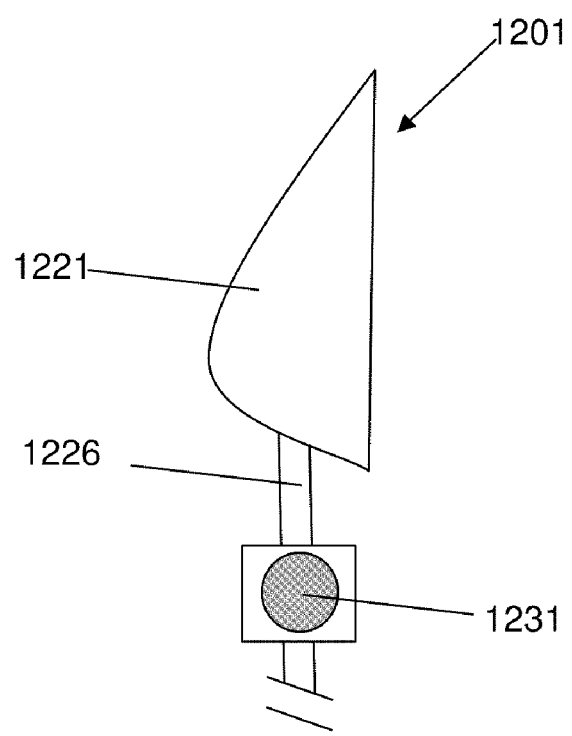

FIGS. 22A and 22B show alternate embodiments of a breathing mask 1200 and 1201, respectively, comprising a mask portion 1220 and 1221, respectively, and a gas feeder tube 1225 and 1226, respectively. In FIG. 22A, sensor device 1230 is integral with the mask portion 1220, while in FIG. 2B, sensor device 1231 is shown in-line with the gas feeder tube 1226.

Whereas particular embodiments of this invention have been described above for purposes of illustration, it will be evident to those skilled in the art that numerous variations of the details of the present invention may be made without departing from the invention as defined in the appended claims.

We claim:

1. A capacitive sensor, comprising:
   a. a semiconductor substrate having a well; and
   b. one or more conductor pairs attached to the substrate at an attachment point and extending over the well, defining an air gap between the conductor pair and the substrate, each conductor pair comprising a first and second conductor spaced-apart to define a capillary gap and further comprising a chemical-sensitive polymer dielectric material or a chemical-sensitive nanocomposite dielectric material in the capillary gap.

2. The sensor of claim 1, in which the chemical-sensitive polymer dielectric material or chemical-sensitive nanocomposite dielectric material is a polymer dielectric material.

3. The sensor of claim 2, in which the polymer dielectric material is a polyimide.

4. The sensor of claim 2, in which the polymer dielectric material is selected from the group consisting of polyimide, polymethyl methacrylate (PMMA), poly(ethylene teraphthalate) (PET), polysulfone (PSF), cellulose acetate butyrate (CAB), polyethynyl fluorenol (PEFI), poly(dimethyl siloxane (PDMS) and poly(etherurethane) (PEUT).

5. The sensor of claim 1, wherein each conductor of the one or more conductor pairs has an inward-facing side that faces the substrate and an outward-facing side opposite the inward-facing side, and the chemical-sensitive polymer dielectric material or chemical-sensitive nanocomposite dielectric material covers the outward-facing side of the conductors.

6. The sensor of claim 1, wherein the conductors are beams suspended over the well.

7. The sensor of claim 6, in which the beams are at least 100 µm long.

8. The sensor of claim 6, in which the beams are 150 µm long.

9. The sensor of claim 1, wherein each conductor of the one or more conductor pairs has an inward-facing side that faces the substrate and an outward-facing side opposite the inward-facing side, the sensor further comprising the chemical-sensitive polymer dielectric material or chemical-sensitive nanocomposite dielectric material on the inward-facing side of the conductor pairs.

10. The sensor of claim 9, wherein the well is filled with the chemical-sensitive polymer dielectric material or chemical-sensitive nanocomposite dielectric material, covering the conductor pairs with the chemical-sensitive polymer dielectric material or chemical-sensitive nanocomposite dielectric material.

11. The sensor of claim 1, comprising a plurality of conductor pairs, wherein the plurality of conductor pairs are supported by one or more trusses extending between the conductors and the conductor pairs.

12. The sensor of claim 1, the substrate further comprising an inkjet well and the capillary gaps of the one or more conductor pairs opens into the inkjet well such that a solution comprising a chemical-sensitive polymer dielectric material or chemical-sensitive nanocomposite dielectric material deposited into the inkjet well is drawn into the capillary gap.

13. The sensor of claim 1, wherein each conductor comprises two or more metal layers separated by an insulator and electrically connected to each-other at one or more points.

14. The sensor of claim 13, wherein the insulator is silicon dioxide.

15. A sensing apparatus comprising the sensor as claimed in claim 1 and a sensor computing device.

16. The sensing apparatus of claim 15, contained in a gas mask.

17. The sensor of claim 1, in which the chemical-sensitive polymer dielectric material or chemical-sensitive nanocomposite dielectric material is a nanocomposite.

18. The sensor of claim 17, in which the nanocomposite comprises one of a nanoparticle, a nanocluster or a nanocrystalline material.

19. The sensor of claim 17, in which the nanocomposite comprises one of a silicon nanocluster, a metal nanocluster, a gold nanocluster, a mesoporous silica, a mesoporous ceramic material or an aerogel.

20. The sensor of claim 17, in which the nanocomposite comprises a nanocluster or nanoparticle capped with a carbon containing thiol moiety.

* * * * *

UNITED STATES PATENT AND TRADEMARK OFFICE
CERTIFICATE OF CORRECTION

PATENT NO. : 8,410,562 B2  Page 1 of 1
APPLICATION NO. : 13/010954
DATED : April 2, 2013
INVENTOR(S) : Nathan Scott Lazarus et al.

It is certified that error appears in the above-identified patent and that said Letters Patent is hereby corrected as shown below:

On the Title Page

Column 2, Item (74) Attorney, Agent, or Firm, Line 1, delete "The Web Law Firm" and insert -- The Webb Law Firm --

In the Claims

Column 13, Lines 35-36, Claim 4, delete "teraphthalate)" and insert -- terephthalate --

Signed and Sealed this
Second Day of July, 2013

Teresa Stanek Rea
*Acting Director of the United States Patent and Trademark Office*